US006969529B2

(12) United States Patent
Bosch et al.

(10) Patent No.: US 6,969,529 B2
(45) Date of Patent: *Nov. 29, 2005

(54) NANOPARTICULATE COMPOSITIONS COMPRISING COPOLYMERS OF VINYL PYRROLIDONE AND VINYL ACETATE AS SURFACE STABILIZERS

(75) Inventors: H. William Bosch, Bryn Mawr, PA (US); Niels P. Ryde, Malvern, PA (US)

(73) Assignee: Elan Pharma International Ltd., Dublin (IE)

( * ) Notice: Subject to any disclaimer, the term of this patent is extended or adjusted under 35 U.S.C. 154(b) by 0 days.

This patent is subject to a terminal disclaimer.

(21) Appl. No.: 10/345,312

(22) Filed: Jan. 16, 2003

(65) Prior Publication Data

US 2003/0108616 A1   Jun. 12, 2003

Related U.S. Application Data

(63) Continuation of application No. 09/715,117, filed on Nov. 20, 2000, now abandoned, and a continuation-in-part of application No. 10/075,443, filed on Feb. 15, 2002, now Pat. No. 6,592,903, which is a continuation of application No. 09/666,539, filed on Sep. 21, 2000, now Pat. No. 6,375,986.

(51) Int. Cl.[7] .......................... A61K 9/14; A61K 9/48; A61K 9/20
(52) U.S. Cl. ...................... 424/489; 424/451; 424/464
(58) Field of Search ............................... 424/489, 490, 424/497, 484, 400, 451, 464

(56) References Cited

U.S. PATENT DOCUMENTS

| | | |
|---|---|---|
| 4,540,602 A | 9/1985 | Motoyama et al. |
| 4,727,077 A | 2/1988 | Haga et al. |
| 4,783,484 A | 11/1988 | Violante et al. |
| 4,826,689 A | 5/1989 | Violante et al. |
| 4,851,421 A | 7/1989 | Iwasaki et al. |
| 4,904,668 A | 2/1990 | Kondo et al. |
| 4,983,605 A | 1/1991 | Kondo et al. |
| 4,997,454 A | 3/1991 | Violante et al. |
| 5,002,952 A | 3/1991 | Kondo et al. |
| 5,098,907 A | 3/1992 | Kondo et al. |
| 5,118,528 A | 6/1992 | Fessi et al. |
| 5,145,684 A * | 9/1992 | Liversidge et al. ......... 424/489 |
| 5,264,213 A | 11/1993 | Shibahara et al. |
| 5,298,262 A | 3/1994 | Na et al. |
| 5,302,401 A | 4/1994 | Liversidge et al. |
| 5,318,767 A | 6/1994 | Liversidge et al. |
| 5,326,552 A | 7/1994 | Na et al. |
| 5,336,507 A | 8/1994 | Na et al. |
| 5,346,702 A | 9/1994 | Na et al. |
| 5,352,459 A | 10/1994 | Hollister et al. |
| 5,399,363 A | 3/1995 | Liversidge et al. |
| 5,401,492 A | 3/1995 | Kellar et al. |
| 5,429,824 A | 7/1995 | June |
| 5,447,710 A | 9/1995 | Na et al. |
| 5,451,393 A | 9/1995 | Liversidge et al. |
| 5,466,433 A | 11/1995 | Bacon et al. |
| 5,466,440 A | 11/1995 | Ruddy et al. |
| 5,470,583 A | 11/1995 | Na et al. |
| 5,472,683 A | 12/1995 | Illig |
| 5,494,683 A | 2/1996 | Liversidge et al. |
| 5,500,204 A | 3/1996 | Osifo et al. |
| 5,503,723 A | 4/1996 | Ruddy et al. |
| 5,510,118 A | 4/1996 | Bosch et al. |
| 5,518,187 A | 5/1996 | Bruno et al. |
| 5,518,738 A | 5/1996 | Eickhoff et al. |
| 5,521,218 A | 5/1996 | Osifo |
| 5,525,328 A | 6/1996 | Bacon et al. |
| 5,534,270 A | 7/1996 | De Castro |
| 5,543,133 A | 8/1996 | Swanson et al. |
| 5,552,160 A * | 9/1996 | Liversidge et al. ......... 424/489 |
| 5,560,931 A | 10/1996 | Eickhoff et al. |
| 5,560,932 A | 10/1996 | Bagchi et al. |
| 5,565,188 A | 10/1996 | Wong et al. |
| 5,569,448 A | 10/1996 | Wong et al. |
| 5,571,536 A | 11/1996 | Eickhoff et al. |
| 5,573,749 A | 11/1996 | Illig |
| 5,573,750 A | 11/1996 | Singh |
| 5,580,579 A | 12/1996 | Ruddy et al. |
| 5,585,108 A | 12/1996 | Ruddy et al. |
| 5,587,143 A | 12/1996 | Wong |
| 5,591,456 A | 1/1997 | Franson et al. |
| 5,593,657 A | 1/1997 | Ruddy et al. |
| 5,595,762 A * | 1/1997 | Derrieu et al. .............. 424/490 |

(Continued)

FOREIGN PATENT DOCUMENTS

EP          0 262 560          9/1987

(Continued)

OTHER PUBLICATIONS

Matsumoto et al., "Physical Properties of Solid Molecular dispersions of Indomethacin with Poly(vinylpyrrolidone) and Poly(vinylpyrrolidone-co-vinyl-acetate) in Relation to Indomethacin Crystallization," *Pharmaceutical Research* (1999), vol. 16, No. 11, pp. 1722-1728, XP000987250.

(Continued)

*Primary Examiner*—Thuman K. Page
*Assistant Examiner*—Humera N. Sheikh
(74) *Attorney, Agent, or Firm*—Foley & Lardner LLP

(57) ABSTRACT

The present invention is directed to nanoparticulate compositions comprising a poorly soluble drug and at least one copolymer of vinyl pyrrolidone and vinyl acetate as a surface stabilizer adsorbed to the surface of the drug. Also encompassed by the invention are pharmaceutical compositions comprising a nanoparticulate composition of the invention, methods of making and using such nanoparticulate and pharmaceutical compositions.

38 Claims, No Drawings

U.S. PATENT DOCUMENTS

| | | | |
|---|---|---|---|
| 5,603,916 | A | 2/1997 | Singh |
| 5,622,938 | A | 4/1997 | Wong |
| 5,628,981 | A | 5/1997 | Liversidge et al. |
| 5,643,552 | A | 7/1997 | Illig |
| 5,662,883 | A | 9/1997 | Bagchi et al. |
| 5,665,330 | A | 9/1997 | Wong |
| 5,665,331 | A | 9/1997 | Bagchi et al. |
| 5,668,196 | A | 9/1997 | Robinson et al. |
| 5,670,136 | A | 9/1997 | Bacon et al. |
| 5,716,642 | A | 2/1998 | Bagchi et al. |
| 5,718,388 | A | 2/1998 | Czekai et al. |
| 5,718,919 | A | 2/1998 | Ruddy et al. |
| 5,741,522 | A | 4/1998 | Violante et al. |
| 5,747,001 | A | 5/1998 | Wiedmann et al. |
| 5,776,496 | A | 7/1998 | Violante et al. |
| 5,834,025 | A | 11/1998 | de Garavilla et al. |
| 5,862,999 | A | 1/1999 | Czekai et al. |
| 5,891,420 | A | 4/1999 | Cutie |
| 5,972,389 | A | 10/1999 | Shell et al. |
| 6,045,829 | A | 4/2000 | Liversidge et al. |
| 6,068,858 | A | 5/2000 | Liversidge et al. |
| 6,153,225 | A | 11/2000 | Lee et al. |
| 6,165,506 | A | 12/2000 | Jain et al. |
| 6,264,922 | B1 | 7/2001 | Wood et al. |
| 6,375,986 | B1 * | 4/2002 | Ryde et al. .................. 424/489 |
| 6,592,903 | B2 * | 7/2003 | Ryde et al. .................. 424/489 |

FOREIGN PATENT DOCUMENTS

| | | | | |
|---|---|---|---|---|
| EP | 0 818 450 | A1 | 1/1998 | |
| WO | WO 93/13773 | A1 | 7/1993 | |
| WO | WO 9313773 | A1 * | 7/1993 | ............ A61K 9/16 |
| WO | 96/25918 | | 8/1996 | |
| WO | 98/35666 | | 8/1998 | |
| WO | 00/18374 | | 4/2000 | |
| WO | 00/27363 | | 5/2000 | |
| WO | WO 02/24163 | A1 | 3/2002 | |

OTHER PUBLICATIONS

Hülsmann et al., "Melt extrusion—an alternative method for enhancing the dissolution rate of 17β-estradiol hemihydrate," *European Journal of Pharmaceutics and Biopharmaceutics* (2000), vol. 49, No. 3, pp. 237-242, XP004257163.

Vojnovic et al., "Formulation and evaluation of vinylpyrolidone/vinylacetate copolymer microspheres and griseofuvin," *J. Microencapsulation* (1993), vol. 10, No. 1, pp. 89-99, XP000334996.

Bogdanova et al., "Solid Dispersions of Isopropylantipyrin," *Labo-Pharma-Probl. Tech.* (1984), vol. 32, No. 348, pp. 835-837, XP001097528.

Zingone et al., "Characterization and dissolution study of solid dispersions of theophylline and indomethacin with PVP/VA copolymers," *STP Pharma Sciences* (1992), vol. 2, No. 2, pp. 186-192, XP002111752.

Kondo et al., "Improved Oral Absorption of Enteric Coprecipitates of a Poorly Soluble Drug," *Journal of Pharmaceutical Sciences* vol. 83, No. 4, Apr. 1994, pp. 566-570.

Kondo et al., "Improved Oral Absorption of a Poorly Water-Soluble Drug, HO-221, by Wet Bead Milling Producing Particles in Submicron Region," *Chemical & Pharmaceutical Bulletin* vol. 41, No. 4, Apr. 1993, pp. 737-740.

Kondo et al., "Pharmacokinetics of a Micronized, Poorly Water-Soluble Drug, HO-221, in Experimental Animals," *Biological & Pharmaceutical Bulletin* vol. 16, No. 8, Aug. 1993, pp. 796-800.

Plasdone® Povidone USP Technical Profile, International Specialty Products, 1999.

Plasdone® S-630 Technical Profile, International Speciality Products, 2000.

Kollidon® Grades Sheet, BASF.

* cited by examiner

NANOPARTICULATE COMPOSITIONS COMPRISING COPOLYMERS OF VINYL PYRROLIDONE AND VINYL ACETATE AS SURFACE STABILIZERS

CROSS-REFERENCE TO RELATED PATENT APPLICATIONS

This application is a Continuation of U.S. application Ser. No. 09/715,117, filed Nov. 20, 2000 now abandoned, incorporated herein by reference in its entirety. This application is also a Continuation-in-part of U.S. application Ser. No. 10/075,443, filed Feb. 15, 2002 now U.S. Pat. No. 6,592,903, incorporated herein by reference in its entirety, which is a Continuation of U.S. application Ser. No. 09/666,539, filed Sep. 21, 2000, now U.S. Pat. No. 6,375,986, issued Apr. 23, 2002, incorporated herein by reference in its entirety.

FIELD OF THE INVENTION

The present invention is directed to nanoparticulate formulations of a drug having at least one copolymer of vinyl pyrrolidone and vinyl acetate adsorbed on the surface of the drug as a surface stabilizer, and methods of making and using such compositions.

BACKGROUND OF THE INVENTION

Nanoparticulate compositions, first described in U.S. Pat. No. 5,145,684 ("the '684 patent"), are particles consisting of a poorly soluble therapeutic or diagnostic agent having adsorbed onto the surface thereof a non-crosslinked surface stabilizer. The '684 patent describes the use of a variety of surface stabilizers for nanoparticulate compositions. The use of a copolymer of vinyl pyrrolidone and vinyl acetate as a surface stabilizer for nanoparticulate compositions, or any other component of such compositions, is not described by the '684 patent.

The '684 patent describes a method of screening drugs to identify useful surface stabilizers that enable the production of a nanoparticulate composition. Not all surface stabilizers will function to produce a stable, non-agglomerated nanoparticulate composition for all drugs. Moreover, known surface stabilizers may be unable to produce a stable, non-agglomerated nanoparticulate composition for certain drugs. Thus, there is a need in the art to identify new surface stabilizers useful in making nanoparticulate compositions. Additionally, such new surface stabilizers may have superior properties over prior known surface stabilizers.

There is a need in the art for new surface stabilizers for nanoparticulate compositions of poorly soluble drugs. In addition, there is a need in the art for surface stabilizers useful in preparing nanoparticulate compositions of drugs, in which prior known surface stabilizers are ineffective. The present invention satisfies these needs.

SUMMARY OF THE INVENTION

The present invention is directed to nanoparticulate compositions comprising a poorly soluble drug and at least one copolymer of vinyl pyrrolidone and vinyl acetate as a surface stabilizer adsorbed to the surface of the drug.

Another aspect of the invention is directed to pharmaceutical compositions comprising a nanoparticulate composition of the invention. The pharmaceutical composition preferably comprises a poorly soluble drug, at least one copolymer of vinyl pyrrolidone and vinyl acetate as a surface stabilizer adsorbed to the surface of the drug, and a pharmaceutically acceptable carrier, as well as any desired excipients.

This invention further discloses a method of making a nanoparticulate composition having at least one copolymer of vinyl pyrrolidone and vinyl acetate as a surface stabilizer adsorbed on the surface of the drug. Such a method comprises contacting a poorly soluble nanoparticulate drug with at least one copolymer of vinyl pyrrolidone and vinyl acetate as a surface stabilizer for a time and under conditions sufficient to provide a nanoparticle/copolymer composition. The copolymer surface stabilizers can be contacted with the drug either before, during, or after size reduction of the drug.

The present invention is further directed to a method of treatment comprising administering to a mammal in need a therapeutically effective amount of a nanoparticulate drug/copolymer composition according to the invention.

Both the foregoing general description and the following detailed description are exemplary and explanatory and are intended to provide further explanation of the invention as claimed. Other objects, advantages, and novel features will be readily apparent to those skilled in the art from the following detailed description of the invention.

DETAILED DESCRIPTION OF THE PREFERRED EMBODIMENTS

The present invention is directed to a composition comprising nanoparticulate drug having at least one copolymer of vinyl pyrrolidone and vinyl acetate as a surface stabilizer adsorbed on the surface thereof, and methods of making and using such nanoparticulate compositions.

A. Compositions

The compositions of the invention comprise nanoparticulate drug and at least one copolymer of vinyl pyrrolidone and vinyl acetate as a surface stabilizer adsorbed to the surface of the drug. Surface stabilizers useful herein physically adhere to the surface of the nanoparticulate drug, but do not chemically react with the drug or itself. Individually adsorbed molecules of the surface stabilizer are essentially free of intermolecular cross-linkages.

The present invention also includes nanoparticulate compositions having at least one copolymer of vinyl pyrrolidone and vinyl acetate as a surface stabilizer adsorbed on the surface thereof, formulated into compositions together with one or more non-toxic physiologically acceptable carriers, adjuvants, or vehicles, collectively referred to as carriers. The compositions can be formulated for parenteral injection, oral administration in solid or liquid form, rectal or topical administration, and the like.

1. Drug Particles

The nanoparticles of the invention comprise a therapeutic or diagnostic agent, collectively referred to as a "drug." A therapeutic agent can be a pharmaceutical agent, including biologics such as proteins, peptides, and nucleotides, or a diagnostic agent, such as a contrast agent, including x-ray contrast agents. The drug exists either as a discrete, crystalline phase, or as an amorphous phase. The crystalline phase differs from a non-crystalline or amorphous phase which results from precipitation techniques, such as those described in EP Patent No. 275,796.

The invention can be practiced with a wide variety of drugs. The drug is preferably present in an essentially pure form, is poorly soluble, and is dispersible in at least one liquid medium. By "poorly soluble" it is meant that the drug has a solubility in the liquid dispersion medium of less than about 10 mg/mL, and preferably of less than about 1 mg/mL.

The drug can be selected from a variety of known classes of drugs, including, for example, proteins, peptides, nucleotides, anti-obesity drugs, nutriceuticals, corticosteroids, elastase inhibitors, analgesics, antifungals, oncology therapies, anti-emetics, analgesics, cardiovascular agents, anti-inflammatory agents, anthelmintics, anti-arrhythmic agents, antibiotics (including penicillins), anticoagulants, antidepressants, antidiabetic agents, antiepileptics, antihistamines, antihypertensive agents, antimuscarinic agents, antimycobacterial agents, antineoplastic agents, immunosuppressants, antithyroid agents, antiviral agents, anxiolytic sedatives (hypnotics and neuroleptics), astringents, beta-adrenoceptor blocking agents, blood products and substitutes, cardiac inotropic agents, contrast media, corticosteroids, cough suppressants (expectorants and mucolytics), diagnostic agents, diagnostic imaging agents, diuretics, dopaminergics (antiparkinsonian agents), haemostatics, immuriological agents, lipid regulating agents, muscle relaxants, parasympathomimetics, parathyroid calcitonin and biphosphonates, prostaglandins, radio-pharmaceuticals, sex hormones (including steroids), anti-allergic agents, stimulants and anoretics, sympathomimetics, thyroid agents, vasodilators and xanthines.

The drugs are commercially available and/or can be prepared by techniques known in the art.

2. Copolymer Surface Stabilizers

Commercially available copolymers of vinyl pyrrolidone and vinyl acetate are Plasdone® S630 (ISP) and Kollidon® VA 64 (BASF), which contain vinyl pyrrolidone and vinyl acetate in a 60:40 ratio. Other copolymers of vinyl pyrrolidone and vinyl acetate can also be used in the invention. Preferably, the copolymer contains at least 40% vinyl pyrrolidone, although smaller amounts of vinyl pyrrolidone can also be utilized. Other useful copolymers contain vinyl pyrrolidone and vinyl acetate in ratios of, for example, 90:10, 80:20, 70:30, and 50:50. The amount of vinyl pyrrolidone can range from about 40% up to about 99.9%, and the amount of vinyl acetate can range from about 0.1% up to about 60%.

Two or more surface stabilizers can be used in combination.

3. Auxiliary Surface Stabilizers

The compositions of the invention can also include one or more auxiliary surface stabilizers in addition to the at least one copolymer of vinyl pyrrolidone and vinyl acetate. Suitable auxiliary surface stabilizers can preferably be selected from known organic and inorganic pharmaceutical excipients. Such excipients include various polymers, low molecular weight oligomers, natural products, and surfactants. Preferred surface stabilizers include nonionic and ionic surfactants. Two or more surface auxiliary stabilizers can be used in combination.

Representative examples of auxiliary surface stabilizers include cetyl pyridinium chloride, gelatin, casein, lecithin (phosphatides), dextran, glycerol, gum acacia, cholesterol, tragacanth, stearic acid, benzalkonium chloride, calcium stearate, glycerol monostearate, cetostearyl alcohol, cetomacrogol emulsifying wax, sorbitan esters, polyoxyethylene alkyl ethers (e.g., macrogol ethers such as cetomacrogol 1000), polyoxyethylene castor oil derivatives, polyoxyethylene sorbitan fatty acid esters (e.g., the commercially available Tweens® such as e.g., Tween 20® and Tween 80® (ICI Specialty Chemicals)); polyethylene glycols (e.g., Carbowaxes 3350® and 1450®, and Carbopol 934® (Union Carbide)), dodecyl trimethyl ammonium bromide, polyoxyethylene stearates, colloidal silicon dioxide, phosphates, sodium dodecylsulfate, carboxymethylcellulose calcium, hydroxypropyl celluloses (e.g., HPC, HPC-SL, and HPC-L), hydroxypropyl methylcellulose (HPMC), carboxymethylcellulose sodium, methylcellulose, hydroxyethylcellulose, hydroxypropylmethyl-cellulose phthalate, noncrystalline cellulose, magnesium aluminum silicate, triethanolamine, polyvinyl alcohol (PVA), polyvinylpyrrolidone (PVP), 4-(1,1,3,3-tetramethylbutyl)-phenol polymer with ethylene oxide and formaldehyde (also known as tyloxapol, superione, and triton), poloxamers (e.g., Pluronics F68® and F108®, which are block copolymers of ethylene oxide and propylene oxide); poloxamines (e.g., Tetronic 908®, also known as Poloxamine 908®, which is a tetrafunctional block copolymer derived from sequential addition of propylene oxide and ethylene oxide to ethylenediamine (BASF Wyandotte Corporation, Parsippany, N.J.)); a charged phospholipid such as dimyristoyl phophatidyl glycerol, dioctylsulfosuccinate (DOSS); Tetronic 1508® (T-1508) (BASF Wyandotte Corporation), dialkylesters of sodium sulfosuccinic acid (e.g., Aerosol OT®, which is a dioctyl ester of sodium sulfosuccinic acid (Cytec Industries, West Paterson, N.J.)); Duponol P®, which is a sodium lauryl sulfate (DuPont); Triton X-200®, which is an alkyl aryl polyether sulfonate (Union Carbide); Crodestas F-110®, which is a mixture of sucrose stearate and sucrose distearate (Croda Inc.); p-isononylphenoxypoly-(glycidol), also known as Olin-IOG® or Surfactant 10-G® (Olin Chemicals, Stamford, Conn.); Crodestas SL-40® (Croda, Inc.); decanoyl-N-methylglucamide; n-decyl β-D-glucopyranoside; n-decyl β-D-maltopyranoside; n-dodecyl β-D-glucopyranoside; n-dodecyl β-D-maltoside; heptanoyl-N-methylglucamide; n-heptyl-β-D-glucopyranoside; n-heptyl β-D-thioglucoside; n-hexyl β-D-glucopyranoside; nonanoyl-N-methylglucamide; n-noyl β-D-glucopyranoside; octanoyl-N-methylglucamide; n-octyl-β-D-glucopyranoside; octyl β-D-thioglucopyranoside; and the like.

Most of these surface stabilizers are known pharmaceutical excipients and are described in detail in the *Handbook of Pharmaceutical Excipients*, published jointly by the American Pharmaceutical Association and The Pharmaceutical Society of Great Britain (The Pharmaceutical Press, 2000), specifically incorporated by reference. The surface stabilizers are commercially available and/or can be prepared by techniques known in the art.

4. Nanoparticulate Drug/Copolymer Particle Size

Preferably, the compositions of the invention contain nanoparticles which have an effective average particle size of less than about 2000 nm (i.e., 2 microns), more preferably less than about 1500 nm, less than about 1000 nm, less than about 800 nm, less than about 600 nm, less than about 400 nm, less than about 300 nm, less than about 250 nm, less than about 100 nm, or less than about 50 nm, as measured by light-scattering methods, microscopy, or other appropriate methods. By "an effective average particle size of less than about 2000 nm" it is meant that at least 50% of the drug particles have a particle size of less than about 2000 nm when measured by light scattering techniques. Preferably, at least 70% of the drug particles have a particle size of less than about 2000 nm, more preferably at least 90% of the drug particles have a particle size of less than about 2000 nm, and even more preferably at least about 95% of the particles have a particle size of less than about 2000 nm.

5. Concentration of Nanoparticulate Drug and Stabilizer

The relative amount of drug and one or more surface stabilizers can vary widely. The optimal amount of the surface stabilizers can depend, for example, upon the particular active agent selected, the hydrophilic lipophilic balance (HLB), melting point, and water solubility of the copolymer, and the surface tension of water solutions of the stabilizer, etc.

The concentration of the one or more surface stabilizers can vary from about 0.01 to about 90%, from about 1 to about 75%, from about 10 to about 60%, and from about 10 to about 55% by weight based on the total combined weight of the drug substance and surface stabilizer, not including other excipients.

The concentration of the drug can vary from about 99.9% to about 0.1%, from about 80% to about 5.0%, or from about 50% to about 10%, by weight based on the total combined weight of the drug substance and surface stabilizer, not including other excipients.

B. Methods of Making Nanoparticulate Formulations

The nanoparticulate drug compositions can be made using, for example, milling or precipitation techniques. Exemplary methods of making nanoparticulate compositions are described in the '684 patent. Methods of making nanoparticulate compositions are also described in U.S. Pat. No. 5,518,187, for "Method of Grinding Pharmaceutical Substances;" U.S. Pat. No. 5,718,388, for "Continuous Method of Grinding Pharmaceutical Substances;" U.S. Pat. No. 5,862,999, for "Method of Grinding Pharmaceutical Substances;" U.S. Pat. No. 5,665,331, for "Co-Microprecipitation of Nanoparticulate Pharmaceutical Agents with Crystal Growth Modifiers;" U.S. Pat. No. 5,662,883, for "Co-Microprecipitation of Nanoparticulate Pharmaceutical Agents with Crystal Growth Modifiers;" U.S. Pat. No. 5,560,932, for "Microprecipitation of Nanoparticulate Pharmaceutical Agents;" U.S. Pat. No. 5,543,133, for "Process of Preparing X-Ray Contrast Compositions Containing Nanoparticles;" U.S. Pat. No. 5,534,270, for "Method of Preparing Stable Drug Nanoparticles;" U.S. Pat. No. 5,510,118, for "Process of Preparing Therapeutic Compositions Containing Nanoparticles;" and U.S. Pat. No. 5,470,583, for "Method of Preparing Nanoparticle Compositions Containing Charged Phospholipids to Reduce Aggregation," all of which are specifically incorporated by reference.

1. Milling to obtain Nanoparticulate Drug Dispersions

Milling of aqueous drug to obtain a nanoparticulate dispersion comprises dispersing drug particles in a liquid dispersion medium in which the drug is poorly soluble, followed by applying mechanical means in the presence of grinding media to reduce the particle size of the drug to the desired effective average particle size. The dispersion medium can be, for example, water, safflower oil, ethanol, t-butanol, glycerin, polyethylene glycol (PEG), hexane, or glycol.

The particles can be reduced in size in the presence of at least one copolymer of vinyl pyrrolidone and vinyl acetate surface stabilizer. Alternatively, the particles can be contacted with one or more surface stabilizers after attrition. Other compounds, such as a diluent, can be added to the drug/surface stabilizer composition during the size reduction process. Dispersions can be manufactured continuously or in a batch mode. The resultant nanoparticulate drug dispersion can be utilized in solid or liquid dosage formulations.

2. Precipitation to Obtain Nanoparticulate Drug Compositions

Another method of forming the desired nanoparticulate composition is by microprecipitation. This is a method of preparing stable dispersions of poorly soluble drugs in the presence of one or more surface stabilizers and one or more colloid stability enhancing surface active agents free of any trace toxic solvents or solubilized heavy metal impurities. Such a method comprises, for example: (1) dissolving the poorly soluble drug in a suitable solvent; (2) adding the formulation from step (1) to a solution comprising at least one copolymer surface stabilizer to form a clear solution; and (3) precipitating the formulation from step (2) using an appropriate non-solvent. The method can be followed by removal of any formed salt, if present, by dialysis or diafiltration and concentration of the dispersion by conventional means. The resultant nanoparticulate drug dispersion can be utilized in solid or liquid dosage formulations.

C. Methods of Using Nanoparticulate Drug Formulations Comprising One or More Surface Stabilizers The nanoparticulate compositions of the present invention can be administered to humans and animals via any conventional means, including but not limited to orally, rectally, parenterally (intravenous, intramuscular, or subcutaneous), intracisternally, pulmonary, intravaginally, intraperitoneally, locally (powders, ointments or drops), or as a buccal or nasal spray.

Compositions suitable for parenteral injection may comprise physiologically acceptable sterile aqueous or nonaqueous solutions, dispersions, suspensions or emulsions and sterile powders for reconstitution into sterile injectable solutions or dispersions. Examples of suitable aqueous and nonaqueous carriers, diluents, solvents, or vehicles including water, ethanol, polyols (propyleneglycol, polyethyleneglycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions, and by the use of surfactants.

The nanoparticulate compositions may also contain adjuvants such as preserving, wetting, emulsifying, and dispensing agents. Prevention of the growth of microorganisms can be ensured by various antibacterial and antifungal agents, such as parabens, chlorobutanol, phenol, sorbic acid, and the like. It may also be desirable to include isotonic agents, such as sugars, sodium chloride, and the like. Prolonged absorption of the injectable pharmaceutical form can be brought about by the use of agents delaying absorption, such as aluminum monostearate and gelatin.

Solid dosage forms for oral administration include capsules, tablets, pills, powders, and granules. In such solid dosage forms, the active compound is admixed with at least one of the following: (a) one or more inert excipients (or carrier), such as sodium citrate or dicalcium phosphate; (b) fillers or extenders, such as starches, lactose, sucrose, glucose, mannitol, and silicic acid; (c) binders, such as carboxymethylcellulose, alignates, gelatin, polyvinylpyrrolidone, sucrose and acacia; (d) humectants, such as glycerol; (e) disintegrating agents, such as agar-agar, calcium carbonate, potato or tapioca starch, alginic acid, certain complex silicates, and sodium carbonate; (f) solution retarders, such as paraffin; (g) absorption accelerators, such as quaternary ammonium compounds; (h) wetting agents, such as cetyl alcohol and glycerol monostearate; (i) adsorbents, such as kaolin and bentonite; and (j) lubricants, such as talc, calcium stearate, magnesium stearate, solid polyethylene glycols, sodium lauryl sulfate, or mixtures thereof. For capsules, tablets, and pills, the dosage forms may also comprise buffering agents.

Liquid dosage forms for oral administration include pharmaceutically acceptable emulsions, solutions, suspensions, syrups, and elixirs. In addition to the active compounds, the liquid dosage forms may comprise inert diluents commonly used in the art, such as water or other solvents, solubilizing agents, and emulsifiers. Exemplary emulsifiers are ethyl alcohol, isopropyl alcohol, ethyl carbonate, ethyl acetate, benzyl alcohol, benzyl benzoate, propyleneglycol, 1,3-butyleneglycol, dimethylformamide, oils, such as cottonseed oil, groundnut oil, corn germ oil, olive oil, castor oil, and sesame oil, glycerol, tetrahydrofurfuryl alcohol, polyethyleneglycols, fatty acid esters of sorbitan, or mixtures of these substances, and the like.

Besides such inert diluents, the composition can also include adjuvants, such as wetting agents, emulsifying and suspending agents, sweetening, flavoring, and perfuming agents.

Actual dosage levels of active ingredients in the nanoparticulate compositions of the invention may be varied to obtain an amount of active ingredient that is effective to obtain a desired therapeutic response for a particular composition and method of administration. The selected dosage level therefore depends upon the desired therapeutic effect, the route of administration, the potency of the administered drug, the desired duration of treatment, and other factors.

The total daily dose of the compounds of this invention administered to a host in single or divided dose may be in amounts of, for example, from about 1 nanomol to about 50 micromoles per kilogram of body weight. Dosage unit compositions may contain such amounts of such submultiples thereof as may be used to make up the daily dose. It will be understood, however, that the specific dose level for any particular patient will depend upon a variety of factors including the body weight, general health, sex, diet, time and route of administration, potency of the administered drug, rates of absorption and excretion, combination with other drugs and the severity of the particular disease being treated.

The following examples are given to illustrate the present invention. It should be understood, however, that the invention is not to be limited to the specific conditions or details described in these examples. Throughout the specification, any and all references to a publicly available document, including a U.S. patent, are specifically incorporated by reference.

EXAMPLE 1

The purpose of this example was to prepare a nanoparticulate dispersion of a naproxen composition comprising a copolymer of vinyl pyrrolidone and vinyl acetate. Naproxen is a non-steroidal anti-inflammatory drug (NSAID) used in the treatment of rheumatoid conditions.

5% (w/w) of naproxen and 1% Plasdone® S-630 (60% vinyl pyrrolidone, 40% vinyl acetate) (ISP Technologies, Inc.) was milled using a Dyno® Mill (Type: KDL; Mfg.: Willy A Bachofen A G, Basel Switzerland) equipped with a 150 cc batch chamber using a 500 µm milling media (PolyMill® 500; bow Chemical) for 2 hrs at ca. 10° C.

Following milling, the nanoparticulate naproxen dispersion had a mean particle size of 96 nm, with 90% of the particles having a size of less than 141 nm.

EXAMPLE 2

The purpose of this example was to prepare a nanoparticulate dispersion of a nifedipine composition comprising a copolymer of vinyl pyrrolidone and vinyl acetate. Nifedipine is a poorly water-soluble calcium channel blocking agent. The drug affects the movement of calcium into heart and blood vessel cells, and causes a relaxing effect of the muscles to allow an increased amount of blood flow into the heart. Nifedipine is useful in treating angina pectoris (chest pain), and to help reduce blood pressure (antihypertensive).

An aqueous solution of 1% Plasdone® S-630 (60% vinyl pyrrolidone and 40% vinyl acetate) (ISP Technologies, Inc.) and 0.05% sodium lauryl sulfate (SLS) (Spectrum) was prepared by dissolving 0.85 g of polymer and 4.59 g of a 1% SLS solution in 75.66 g of deionized water. The stabilizer solution was mixed with 4.25 g of nifedipine (5% w/w) and charged into the chamber of a DYNO®-Mill Type KDL media mill (Willy Bachofen A G, Basel, Switzerland) along with 500 micron polymeric media (PolyMill® 500; Dow Chemical). The mill was operated for 2 hours and yielded a stable colloidal dispersion of drug substance having a mean particle size of 132 nm, with 90% of the particles having a size of less than 193 nm.

EXAMPLE 3

The purpose of this example was to prepare a nanoparticulate dispersion of a ketoprofen composition comprising a copolymer of vinyl pyrrolidone and vinyl acetate. Ketoprofen is a nonsteroidal anti-inflammatory drug (NSAID) effective in treating fever, pain, and inflammation in the body.

An aqueous solution of 1% Plasdone® S-630 (60% vinyl pyrrolidone and 40% vinyl acetate) (ISP Technologies, Inc.) and 0.05% sodium lauryl sulfate (SLS) (Spectrum) was prepared by dissolving 0.85 g of polymer and 4.26 g of a 1% SLS solution in 75.71 g of deionized water. The stabilizer solution was mixed with 4.25 g of ketoprofen (Wyckoff; 5% w/w) and charged into the chamber of a DYNO®-Mill Type KDL media mill (Willy Bachofen A G, Basel, Switzerland) along with 500 micron polymeric media (PolyMill® 500; Dow Chemical). The mill was operated for 1 hour and yielded a stable colloidal dispersion of drug substance having a mean particle size of 256 nm, with 90% of the particles having a size of less than 355 nm.

EXAMPLE 4

The purpose of this example was to prepare a nanoparticulate dispersion of a triamcinolone acetonide composition comprising a copolymer of vinyl pyrrolidone and vinyl acetate. Triamcinolone acetonide is a corticosteroid used as an antiallergic agent.

An aqueous solution of 1% Plasdone® S-630 (60% vinyl pyrrolidone and 40% vinyl acetate) (ISP Technologies, Inc.) and 0.05% sodium lauryl sulfate (SLS) (Spectrum) was prepared by dissolving 0.85 g of polymer and 4.30 g of a 1% SLS solution in 76.10 g of deionized water. The stabilizer solution was mixed with 4.26 g of triamcinolone acetonide (5% w/w) and charged into the chamber of a DYNO®-Mill Type KDL media mill (Willy Bachofen A G, Basel, Switzerland) along with 500 micron polymeric media (PolyMill® 500; Dow Chemical). The mill was operated for 2 hours and yielded a colloidal dispersion of drug substance having a mean particle size of 121 nm, with 90% of the particles having a size of less than 194 nm.

EXAMPLE 5

The purpose of this example was to prepare a nanoparticulate dispersion of a nanoparticulate diagnostic imaging agent, benzoic acid, 3,5-bis(acetylamino) 2,4,6-triodo, 4-(ethyl-3-ethoxy-2-butenoate) ester (WIN 68209) composition comprising a copolymer of vinyl pyrrolidone and vinyl acetate.

An aqueous solution of 1% of a copolymer of 80% vinyl pyrrolidone and 20% vinyl acetate (Polysciences Inc., Warrington, Pa.) was prepared by dissolving 0.85 g of polymer in 79.91 g of deionized water. The stabilizer solution was mixed with 4.26 g of WIN 68209 (5% drug) and charged into the chamber of a DYNO®-Mill Type KDL media mill (Willy Bachofen A G, Basel, Switzerland) along with 500 micron polymeric media (PolyMill 500; Dow Chemical). The mill was operated for 1 hour and yielded a stable colloidal dispersion of WIN 68209 having a mean particle size of 242 nm, with 90% of the particles having a size of less than 347 nm.

EXAMPLE 6

The purpose of this example was to prepare a nanoparticulate dispersion of a nanoparticulate diagnostic imaging agent, WIN 68209, composition comprising a copolymer of vinyl pyrrolidone and vinyl acetate.

An aqueous solution of 1% of a copolymer of 80% vinyl pyrrolidone and 20% vinyl acetate (Polysciences Inc., Warrington, Pa.) and 1% SLS was prepared by dissolving 0.85 g of polymer and 4.25 g of a 1% SLS solution in 75.67 g of deionized water. The stabilizer solution was mixed with 4.26 g of WIN 68209 (5% drug) and charged into the chamber of a DYNO®-Mill Type KDL media mill (Willy Bachofen A G, Basel, Switzerland) along with 500 micron polymeric media (PolyMill 500; Dow Chemical). The mill was operated for 1 hour and yielded a stable colloidal dispersion of WIN 68209 having a mean particle size of 188 nm, with 90% of the particles having a size of less than 308 nm.

EXAMPLE 7

The purpose of this example was to prepare a nanoparticulate dispersion of a nanoparticulate diagnostic imaging agent, WIN 68209, composition comprising a copolymer of vinyl pyrrolidone and vinyl acetate.

An aqueous solution of 1% of a copolymer of 50% vinyl pyrrolidone and 50% vinyl acetate (Polysciences Inc., Warrington, Pa.) and 0.05% SLS (Spectrum) was prepared by dissolving 0.85 g of polymer and 0.043 g of SLS in 79.86 g of deionized water. The stabilizer solution was mixed with 4.25 g of WIN 68209 (5% drug) and charged into the chamber of a DYNO®-Mill Type KDL media mill (Willy Bachofen A G, Basel, Switzerland) along with 500 micron polymeric media (PolyMill 500; Dow Chemical). The mill was operated for 2 hours and yielded a stable colloidal dispersion of WIN 68209 having a mean particle size of 96 nm, with 90% of the particles having a size of less than 143 nm.

It will be apparent to those skilled in the art that various modifications and variations can be made in the methods and compositions of the present invention without departing from the spirit or scope of the invention. Thus, it is intended that the present invention cover the modifications and variations of this invention provided they come within the scope of the appended claims and their equivalents.

What is claimed is:

1. A stable nanoparticulate drug composition comprising:
   (a) a drug having an effective average particle size of less than about 2000 nm, wherein the drug has a solubility in at least one liquid dispersion medium of less than about 10 mg/mL; and
   (b) at least one copolymer of vinyl pyrrolidone and vinyl acetate adsorbed on the surface thereof as a surface stabilizer.

2. The composition of claim 1, wherein the copolymer of vinyl pyrrolidone and vinyl acetate has from about 40% up to about 99.9% vinyl pyrrolidone and about 0.1% up to about 60% vinyl acetate.

3. The composition of claim 2, wherein the copolymer of vinyl pyrrolidone and vinyl acetate has from about 50% up to about 99.9% vinyl pyrrolidone and about 0.1% up to about 50% vinyl acetate.

4. The composition of claim 2, wherein the copolymer of vinyl pyrrolidone and vinyl acetate has about 60% vinyl pyrrolidone and about 40% vinyl acetate.

5. The composition of claim 2, wherein the copolymer of vinyl pyrrolidone and vinyl acetate has about 80% vinyl pyrrolidone and about 20% vinyl acetate.

6. The composition of claim 1, wherein the drug is present in an amount selected from the group consisting of from about 99.9% to about 0.1%, from about 80% to about 5.0%, and from about 50% to about 10%, by weight based on the total combined weight of the drug substance and surface stabilizer, not including other excipients.

7. The composition of claim 1, wherein at least one copolymer of vinyl pyrrolidone and vinyl acetate is present in an amount selected from the group consisting of from about 0.1 to about 90%, from about 1 to about 75%, from about 10 to about 60%, and from about 10 to about 55%, by weight based on the total combined weight of the drug substance and surface stabilizer, not including other excipients.

8. The composition of claim 1, wherein the drug is selected from the group consisting of a crystalline phase drug and an amorphous phase drug.

9. The composition of claim 1, further comprising at least one surface stabilizer which is not a copolymer of vinyl pyrrolidone and vinyl acetate.

10. The composition of claim 1, comprising two or more copolymers of vinyl pyrrolidone and vinyl acetate.

11. The composition of claim 1, wherein the effective average particle size of the drug present in the nanoparticulate composition is less than about 1500 nm.

12. The composition of claim 11, wherein the effective average particle size of the drug present in the nanoparticulate composition is less than about 1000 nm.

13. The composition of claim 12, wherein the effective average particle size of the drug present in the nanoparticulate composition is less than about 800 nm.

14. The composition of claim 13, wherein the effective average particle size of the drug present in the nanoparticulate composition is less than about 600 nm.

15. The composition of claim 14, wherein the effective average particle size of the drug present in the nanoparticulate composition is less than about 400 nm.

16. The composition of claim 15, wherein the effective average particle size of the drug present in the nanoparticulate composition is less than about 300 nm.

17. The composition of claim 16, wherein the effective average particle size of the drug present in the nanoparticulate composition is less than about 200 nm.

18. The composition of claim 17, wherein the effective average particle size of the drug present in the nanoparticulate composition is less than about 100 nm.

19. The composition of claim 18, wherein the effective average particle size of the drug present in the nanoparticulate composition is less than about 50 nm.

20. A method of treating a patient in need with a stable nanoparticulate drug composition comprising an organic drug, wherein said method comprises:

(a) administering to a mammal in need a therapeutically effective amount of the nanoparticulate drug composition comprising:
  (1) an organic drug having an effective average particle size of less than about 2000 nm wherein the drug has a solubility in at least one liquid dispersion medium of less than about 10 mg/mL; and
  (2) at least one copolymer of vinyl pyrrolidone and vinyl acetate as a surface stabilizer adsorbed on the surface of the drug.

21. The method of claim 20, wherein the copolymer of vinyl pyrrolidone and vinyl acetate has from about 40% up to about 99.9% vinyl pyrrolidone and about 0.1% up to about 60% vinyl acetate.

22. The method of claim 20, wherein the drug is present in an amount selected from the group consisting of from about 99.9% to about 0.1%, from about 80% to about 5.0%, and from about 50% to about 10%, by weight based on the total combined weight of the drug substance and surface stabilizer, not including other excipients.

23. The method of claim 20, wherein the at least one copolymer of vinyl pyrrolidone and vinyl acetate is present in an amount selected from the group consisting of from about 0.1 to about 90%, from about 1 to about 75%, from about 10 to about 60%, and from about 10 to about 55%, by weight based on the total combined weight of the drug substance and surface stabilizer, not including other excipients.

24. The method of claim 20, wherein the drug is selected from the group consisting of a crystalline phase drug and an amorphous phase drug.

25. The method of claim 20, wherein the effective average particle size of the drug present in the nanoparticulate composition is selected from the group consisting of less than about 1500 nm, less than about 1000 nm, less than about 800 nm, less than about 600 nm, less than about 400 nm, less than about 300 nm, less than about 200 nm, less than about 100 nm, and less than about 50 nm.

26. The composition of claim 1, wherein the drug has a solubility in at least one liquid dispersion medium of less than about 1 mg/mL.

27. The composition of claim 1, wherein the liquid dispersion medium is selected from the group consisting of water, safflower oil, ethanol, t-butanol, glycerin, polyethylene glycol (PEG), hexane, and glycol.

28. The composition of claim 1, wherein the drug is selected from the group consisting of proteins, peptides, nucleotides, anti-obesity drugs, nutraceuticals, corticosteroids, elastase inhibitors, analgesics, anti-fungals, oncology therapies, anti-emetics, analgesics, cardiovascular agents, anti-inflammatory agents, anthelmintics, anti-arrhythmic agents, antibiotics, anticoagulants, antidepressants, antidiabetic agents, antiepileptics, antihistamines, antihypertensive agents, antimuscarinic agents, antimycobacterial agents, antineoplastic agents, immunosuppressants, antithyroid agents, antiviral agents, anxiolytic sedatives, astringents, beta-adrenoceptor blocking agents, blood products, blood substitutes, cardiac inotropic agents, contrast media, corticosteroids, cough suppressants, diagnostic agents, diagnostic imaging agents, diuretics, dopaminergics, haemostatics, immunological agents, lipid regulating agents, muscle relaxants, parasympathomimetics, parathyroid calcitonin, parathyroid biphosphonates, prostaglandins, radio-pharmaceuticals, sex hormones, anti-allergic agents, stimulants, anoretics, sympathomimetics, thyroid agents, vasodilators, and xanthines.

29. The composition of claim 1, wherein the drug is selected from the group consisting of naproxen, nifedipine, ketoprofen, triamcinolone acetonide, and WIN 68209.

30. The composition of claim 9, wherein the at least one surface stabilizer which is not a copolymer of vinyl pyrrolidone and vinyl acetate is selected from the group consisting of cetyl pyridinium chloride, gelatin, casein, lecithin, dextran, glycerol, gum acacia, cholesterol, tragacanth, stearic acid, benzalkonium chloride, calcium stearate, glycerol monostearate, cetostearyl alcohol, cetomacrogol emulsifying wax, sorbitan esters, polyoxyethylene alkyl ethers, polyoxyethylene castor oil derivatives, polyoxyethylene sorbitan fatty acid esters, polyethylene glycols, dodecyl trimethyl ammonium bromide, polyoxyethylene stearates, colloidal silicon dioxide, phosphates, sodium dodecylsulfate, carboxymethylcellulose calcium, hydroxypropyl celluloses, hydroxypropyl methylcellulose, carboxymethylcellulose sodium, methylcellulose, hydroxyethylcellulose, hydroxypropylmethyl-cellulose phthalate, noncrystalline cellulose, magnesium aluminum silicate, triethanolamine, polyvinyl alcohol, polyvinylpyrrolidone, tyloxapol, poloxamers, poloxamines, a charged phospholipid, dioctylsulfosuccinate, Tetronic 1508®, dialkylesters of sodium sulfosuccinic acid, sodium lauryl sulfate, an alkyl aryl polyether sulfonate, a mixture of sucrose stearate and sucrose distearate, p-isononylphenoxypoly-(glycidol), Crodestas SL-40®, decanoyl-N-methylglucamide, n-decyl β-D-glucopyranoside, n-decyl β-D-maltopyranoside, n-dodecyl β-D-glucopyranoside, n-dodecyl β-D-maltoside, heptanoyl-N-methylglucamide, n-heptyl-β-D-glucopyranoside, n-heptyl β-D-thioglucoside, n-hexyl β-D-glucopyranoside, nonanoyl-N-methylglucamide, n-noyl β-D-glucopyranoside, octanoyl-N-methylglucamide, n-octyl-β-D-glucopyranoside, and octyl β-D-thioglucopyranoside.

31. The composition of claim 9, wherein the at least one surface stabilizer which is not a copolymer of vinyl pyrrolidone and vinyl acetate is selected from the group consisting of sodium lauryl sulfate and dioctylsulfosuccinate.

32. The method of claim 20, wherein the drug has a solubility in at least one liquid dispersion medium of less than about 1 mg/mL.

33. The method of claim 20, wherein the liquid dispersion medium is selected from the group consisting of water, safflower oil, ethanol, t-butanol, glycerin, polyethylene glycol (PEG), hexane, and glycol.

34. The method of claim 20, wherein the drug is selected from the group consisting of proteins, peptides, nucleotides, anti-obesity drugs, nutraceuticals, corticosteroids, elastase inhibitors, analgesics, anti-fungals, oncology therapies, anti-emetics, analgesics, cardiovascular agents, anti-inflammatory agents, anthelmintics, anti-arrhythmic agents, antibiotics, anticoagulants, antidepressants, antidiabetic agents, antiepileptics, antihistamines, antihypertensive agents, antimuscarinic agents, antimycobacterial agents, antineoplastic agents, immunosuppressants, antithyroid agents, antiviral agents, anxiolytic sedatives, astringents, beta-adrenoceptor blocking agents, blood products, blood substitutes, cardiac inotropic agents, contrast media, corticosteroids, cough suppressants, diagnostic agents, diagnostic imaging agents, diuretics, dopaminergics, haemostatics, immunological agents, lipid regulating agents, muscle relaxants, parasympathomimetics, parathyroid calcitonin, parathyroid biphosphonates, prostaglandins, radio-pharmaceuticals, sex hormones, anti-allergic agents, stimulants, anoretics, sympathomimetics, thyroid agents, vasodilators, and xanthines.

35. The method of claim 20, wherein the drug is selected from the group consisting of naproxen, nifedipine, ketoprofen, triamcinolone acetonide, and WIN 68209.

36. The method of claim 20, wherein the composition further comprises at least one surface stabilizer which is not a copolymer of vinyl pyrrolidone and vinyl acetate.

37. The method of claim 36, wherein the at least one surface stabilizer which is not a copolymer of vinyl pyrrolidone and vinyl acetate is selected from the group consisting of cetyl pyridinium chloride, gelatin, casein, lecithin, dextran, glycerol, gum acacia, cholesterol, tragacanth, stearic acid, benzalkonium chloride, calcium stearate, glycerol monostearate, cetostearyl alcohol, cetomacrogol emulsifying wax, sorbitan esters, polyoxyethylene alkyl ethers, polyoxyethylene castor oil derivatives, polyoxyethylene sorbitan fatty acid esters, polyethylene glycols, dodecyl trimethyl ammonium bromide, polyoxyethylene stearates, colloidal silicon dioxide, phosphates, sodium dodecylsulfate, carboxymethylcellulose calcium, hydroxypropyl celluloses, hydroxypropyl methylcellulose, carboxymethylcellulose sodium, methylcellulose, hydroxyethylcellulose, hydroxypropylmethyl-cellulose phthalate, noncrystalline cellulose, magnesium aluminum silicate, triethanolamine, polyvinyl alcohol, polyvinylpyrrolidone, tyloxapol, poloxamers, poloxamines, a charged phospholipid, dioctylsulfosuccinate, Tetronic 1508®, dialkylesters of sodium sulfosuccinic acid, sodium lauryl sulfate, an alkyl aryl polyether sulfonate, a mixture of sucrose stearate and sucrose distearate, p-isononylphenoxypoly-(glycidol), Crodestas SL-40®, decanoyl-N-methylglucamide, n-decyl β-D-glucopyranoside, n-decyl β-D-maltopyranoside, n-dodecyl β-D-glucopyranoside, n-dodecyl β-D-maltoside, heptanoyl-N-methylglucamide, n-heptyl-β-D-glucopyranoside, n-heptyl β-D-thioglucoside, n-hexyl β-D-glucopyranoside, nonanoyl-N-methylglucamide, n-noyl β-D-glucopyranoside, octanoyl-N-methylglucamide, n-octyl-β-D-glucopyranoside, and octyl β-D-thioglucopyranoside.

38. The method of claim 36, wherein the at least one surface stabilizer which is not a copolymer of vinyl pyrrolidone and vinyl acetate is selected from the group consisting of sodium lauryl sulfate and dioctylsulfosuccinate.

* * * * *